(12) United States Patent
Bahatt et al.

(10) Patent No.: US 7,494,819 B2
(45) Date of Patent: Feb. 24, 2009

(54) ELECTROCHEMILUMINESCENCE ELECTRODE

(75) Inventors: Dar Bahatt, Foster City, CA (US);
Timothy Z. Liu, Fremont, CA (US);
Zbignew Bryning, Campbell, CA (US)

(73) Assignee: Applera Corporation, Foster City, CA (US)

( * ) Notice: Subject to any disclaimer, the term of this patent is extended or adjusted under 35 U.S.C. 154(b) by 596 days.

(21) Appl. No.: 10/866,624

(22) Filed: Jun. 12, 2004

(65) Prior Publication Data

US 2005/0019802 A1    Jan. 27, 2005

Related U.S. Application Data

(60) Provisional application No. 60/478,685, filed on Jun. 13, 2003.

(51) Int. Cl.
*G01N 21/66* (2006.01)
*G01N 21/76* (2006.01)

(52) U.S. Cl. ................. 436/172; 435/6; 204/450; 205/777.5

(58) Field of Classification Search ......... 204/451, 204/450, 290.08, 294; 205/413, 688, 777.5; 436/172; 435/6
See application file for complete search history.

(56) References Cited

U.S. PATENT DOCUMENTS 5,399,247 A    3/1995   Carey et al.
5,578,179 A    11/1996  Demorest et al.
5,776,323 A    7/1998   Kobashi
5,900,127 A    5/1999   Iida et al.
6,267,866 B1   7/2001   Glesener et al.
2002/0029977 A1 3/2002  Natishan et al.
2003/0075445 A1 4/2003  Woudenberg et al.

FOREIGN PATENT DOCUMENTS

EP           0 857 968 A1    12/1998
WO           WO 99/63347     12/1999
WO           WO 00/03233      1/2000

OTHER PUBLICATIONS

International Search Report; PCT / US2004/018663; Filed Jun. 12, 2004; 14 pages.
Arora, Arun, de Mello Andrew J. and Manz, Andreas, *Analytical Communications*, Dec. 1997, vol. 34 (393-395) "Sub-microliter Electrochemiluminescence Detector-A Model for Small Volume Analysis Systems."
Arora, Arun, Eijkel Jan C.T., Morf, Werner E. and Manz, Andreas, *Analytical Chemistry*, Jul. 15, 2001, vol. 73, No. 14, (3282-3288), "A Wireless Electrochemiluminescence Detector Applied to Direct and Indirect Detection for Electrophoresis on a Microfabricated Glass Device."
Arora, Arun, Eijkel Jan C.T., Morf, Werner E. and Manz, Andreas, *Analytical Chemistry*, Nov. 15, 2001, vol. 73, No. 22 (5633) *Correction* "A Wireless Electrochemiluminescene Detector Applied to Direct and Indirect Detection for Electrophoresis on a Microfabricated Glass Device."

*Primary Examiner*—Walter D Griffin
*Assistant Examiner*—Christine T Mui
(74) *Attorney, Agent, or Firm*—Knobbe, Martens, Olson & Bear, LLP (57) ABSTRACT

Disclosed is a bipolar electrode useful for ECL assays and a method for using the same.

30 Claims, 7 Drawing Sheets

ELECTROCHEMILUMINESCENCE ELECTRODE

CROSS-REFERENCE TO RELATED APPLICATION

This application claims the benefit of U.S. Provisional Patent Application No. 60/478,685, filed Jun. 13, 2003, the disclosure of which is incorporated by reference.

BACKGROUND OF THE INVENTION

1. Field of the Invention

The present application relates generally to the detection of molecules, and more particularly, to electrochemiluminescent molecules.

2. Description of the Related Art

Electrochemiluminescence (ECL) is a phenomenon in which a species subjected to a potential at an electrode emits electromagnetic radiation, typically, visible light. A number of ECL-based assays use a bipolar electrode, that is, an electrode not electrically connected to an external circuit. This type of electrode is also known as a floating electrode. In this type of device, an external electric field is applied to an electrolyte containing the bipolar electrode. The external electric field generates anodic and cathodic regions on the floating electrode with respect to the surrounding electrolyte, hence the term bipolar electrode. Published patent applications WO 99/63347 and WO 00/03233, the disclosures of which are incorporated by reference, both disclose ECL-assays using bipolar electrodes.

An ECL detection scheme for capillary electrophoresis (CE) using a bipolar electrode is reported in Arora et al. "A Wireless Electrochemiluminescence Detector Applied to Direct and Indirect Detection for Electrophoresis on a Microfabricated Glass Device" *Anal. Chem.* 2001, 73, 3282-3288, the disclosure of which is incorporated by reference. In one example, the ECL reaction involves an electron transfer from electrochemically generated tripropylamine (TPA) radicals to tris-(2,2'-bipyridyl)ruthenium$^{+3}$ (TBR), which radiates at $\lambda_{max}$=610 nm. A detection limit of $5\times10^{-13}$ M (S/N=3) in an effective volume of 100 nL in a small volume electrochemical cell corresponds to the detection of 30,000 TBR molecules as reported in Arora et al. "Sub-microliter Electrochemiluminescence Detector—A Model for Small Volume Analysis Systems" *Anal. Commun.* 1997, 34, 393-395, the disclosure of which is incorporated by reference.

ECL-based detection in CE has a number of advantages over other detection methods, for example, fluorescence detection. First, no laser excitation source is required because the method is not fluorescence-based. Second, the optical system is simpler and cheaper because the electrode provides a built-in optical alignment. The photodetector is simply aligned with the bipolar electrode. Third, the ECL detection is more sensitive, with no substrate fluorescence or excitation source background. Finally, ECL is automatically initiated by the electric field used to perform CE because the electric field generates the local potential difference at the bipolar electrode.

One problem with an ECL detection system is that electrolysis, for example of water, forms bubbles on and around the bipolar electrode, which distort the bands of the analyte or even occlude the CE channel completely. Where the medium is water, the bubbles are hydrogen and/or oxygen. In other media, the bubbles have other compositions, as is known in the art. Although bubble formation at the electrode is particularly problematic for ECL assays in confined volumes such as CE detectors, the problem is present in all ECL assays using bipolar electrodes. A second problem is that charged species, for example, ECL-active species, accumulating on or around the bipolar electrode increase the background light signal, thereby reducing the sensitivity of the system. The bipolar electrode locally "shorts" the electric field, which slows the migration of charged species in the vicinity of the bipolar electrode, thereby allowing charged species to accumulate on or around the bipolar electrode.

SUMMARY OF THE INVENTION

Disclosed is a bipolar electrode useful for ECL assays and a method for using the same. Some embodiments of the bipolar electrode overcome the problems of bubble formation and/or charged species accumulating at the electrode. Some embodiments of the bipolar electrode are advantageously used in an ECL detector, for example, in a capillary electrophoresis device.

One aspect disclosed herein provides a bipolar electrode useful in ECL assays. The bipolar electrode comprises an electrically conductive first arm, an electrically conductive second arm, and an electrical switch disposed therebetween. In some embodiments, the switch is controlled by a microprocessor or a microcontroller. In some embodiments, the distance between the first arm and the second arm is at least about 20 μm.

In some embodiments, at least one of the first arm or the second arm comprises platinum. In other embodiments, at least one of the first arm or the second arm comprises a material that resists bubble formation. In some embodiments, the potential window of the material in an aqueous medium is at least about 1.5 V, or at least about 2 V. An example of such a material is semiconducting or conducting diamond, for example, boron-doped diamond. Another example of a material that resists bubble formation is a material absorbs hydrogen, for example, palladium. Another example is a metal oxide that absorbs oxygen.

In some embodiments, the bipolar electrode is a component in an electrochemiluminescence detector, wherein the detector further comprises a photodetector. In some embodiments, the electrochemiluminescence detector is a detector in a capillary electrophoresis apparatus. In some embodiments, the capillary electrophoresis apparatus further comprises a microprocessor or microcontroller, wherein the microprocessor or microcontroller controls the switch.

Another aspect provides a method for using a bipolar electrode in detecting an electrochemiluminescent analyte. The method comprises at least the steps of: (a) contacting an electrochemiluminescent analyte with a bipolar electrode, wherein the bipolar electrode comprises an electrically conductive first arm, an electrically conductive second arm, and an electrical switch disposed therebetween; (b) applying an electric field sufficient to initiate an electrochemiluminescent reaction in the analyte at the bipolar electrode; (c) closing the switch; and (d) monitoring for electrochemiluminescence from the analyte. Some embodiments of the method further comprise the steps of: (e) opening the switch; and (f) repeating steps (a) through (e).

In some embodiments, the switch is closed and opened in a cycle that reduces bubble formation on at least one of the first arm or the second arm. In some embodiments, the switch is closed and opened in a cycle that releases charged species on or around at least one of the first arm or the second arm.

In some embodiments, the electrochemiluminescent analyte is contacted with the bipolar electrode using a capillary electrophoresis apparatus, which, in some embodiments, is also used to apply the electric field. In some embodiments, the capillary electrophoresis instrument further comprises a photodetector for monitoring for electrochemiluminescence. In some embodiments, the switch is controlled by a microprocessor or a microcontroller.

In some embodiments, the electrochemiluminescent analyte comprises tris-(2,2'-bipyridyl)ruthenium$^{+3}$. In some embodiments, the ECL reaction further comprises contacting the tris-(2,2'-bipyridyl)ruthenium$^{+3}$ with tripropylamine radical.

In some embodiments, the distance between the first arm and the second arm is at least about 20 µm. In some embodiments, at least one of the first arm or the second arm comprises platinum. In other embodiments, at least one of the first arm or the second arm comprises a material that resists bubble formation. In some embodiments, the potential window of the material in an aqueous medium is at least about 1.5 V, or at least about 2 V. An example of such a material is semiconducting or conducting diamond, for example, boron-doped diamond. Another example of a material that resists bubble formation is a material absorbs hydrogen, for example, palladium. Another example is a metal oxide that absorbs oxygen.

Another aspect provides a bipolar electrode comprising a first electrically conductive arm, a second electrically conductive arm, wherein at least one of the first arm or the second arm independently comprises a material that resists bubble formation.

An example of such a material is boron-doped diamond. Another example is a material that absorbs hydrogen, for example, palladium. Anther example is a metal oxide that absorbs oxygen. In some embodiments, the distance between the first arm and the second arm is at least about 20 µm.

In some embodiments, the bipolar electrode the bipolar electrode is a component in an electrochemiluminescence detector, wherein the detector further comprises a photodetector. In some embodiments, the electrochemiluminescence detector is a detector in a capillary electrophoresis apparatus.

Another aspect provides a method for detecting an electrochemiluminescent analyte comprising at least the steps of: (a) contacting an electrochemiluminescent analyte with a bipolar electrode, wherein the bipolar electrode comprises an electrically conductive first arm, an electrically conductive second arm, wherein at least one of the first arm or second arm independently comprises a material that resists bubble formation; (b) applying an electric field sufficient to initiate an electrochemiluminescent reaction in the analyte at the bipolar electrode; and (c) monitoring for electrochemiluminescence from the analyte. In some embodiments, the method further comprises repeating steps (a) through (c).

In some embodiments, the potential window of the material in an aqueous medium is at least about 1.5 V, or at least about 2 V. An example of such a material is semiconducting or conducting diamond, for example, boron-doped diamond. Another example of a material that resists bubble formation is a material absorbs hydrogen, for example, palladium. Another example is a metal oxide that absorbs oxygen. In some embodiments, the distance between the first arm and the second arm is at least about 20 µm.

In some embodiments, the electrochemiluminescent analyte is contacted with the bipolar electrode using a capillary electrophoresis apparatus. In some embodiments, the capillary electrophoresis apparatus is used to apply the electric field. In some embodiments, the capillary electrophoresis instrument further comprises a photodetector for monitoring for electrochemiluminescence.

In some embodiments, the electrochemiluminescent analyte comprises tris-(2,2'-bipyridyl)ruthenium$^{+3}$. In some embodiments, the ECL reaction further comprises contacting the tris-(2,2'-bipyridyl)ruthenium$^{+3}$ with tripropylamine radical.

DETAILED DESCRIPTION OF THE PREFERRED EMBODIMENTS

Provided herein is an improved bipolar electrode for ECL assays, which, in some embodiments, overcomes the problems of bubbles and/or charged species accumulating on or around a bipolar or floating electrode. In some embodiments, an electrical switch is disposed between the anodic and cathodic regions or arms of the bipolar electrode. In some embodiments, at least a portion of the bipolar electrode is fabricated from a material that resists bubble formation. Some embodiments comprise a bipolar electrode with a switch disposed between the anodic and cathodic regions, wherein at least one of the anodic region or cathodic region is fabricated from a material that resists bubble formation. Although these features are described in the context of ECL detectors for CE systems, the disclosed bipolar electrode is useful in any ECL assay using a bipolar electrode.

Briefly, capillary electrophoresis or CE is a method for separating and/or identifying a compound. A CE apparatus comprises an anode, a cathode, and a capillary tube disposed therebetween. Typically, each end of the capillary tube is fluidly connected to a reservoir into which the anode and cathode are immersed. A suitable electrolyte or matrix, for example, an aqueous medium, is provided in the capillary. Applying a potential between the anode and cathode initiates a flow of the electrolyte, known as an electroosmotic flow (EOF), from one end of the capillary to the other. In a CE apparatus using an unmodified silica capillary, the EOF is from the anode to the cathode. The direction of the EOF is from the cathode to the anode in CE devices using other types of capillaries, for example, modified silica capillaries. The rate at which an analyte travels from one end of the capillary to the other depends on factors known in the art, including size, charge, the composition of the electrolyte, the length and type of capillary, the presence of optional additives, the EOF, and the applied potential. In some embodiments, the analyte travels in the same direction as the EOF. In other embodiments, the analyte travels against the EOF. Because different compounds travel at different rates, CE is used to separate and/or identify compounds. A detector is typically provided at or near the end of the capillary from which the compound or compounds of interest exit. An example of a suitable CE apparatus is disclosed in U.S. Pat. No. 5,578,179, the disclosure of which is incorporated by reference.

Figure 1:
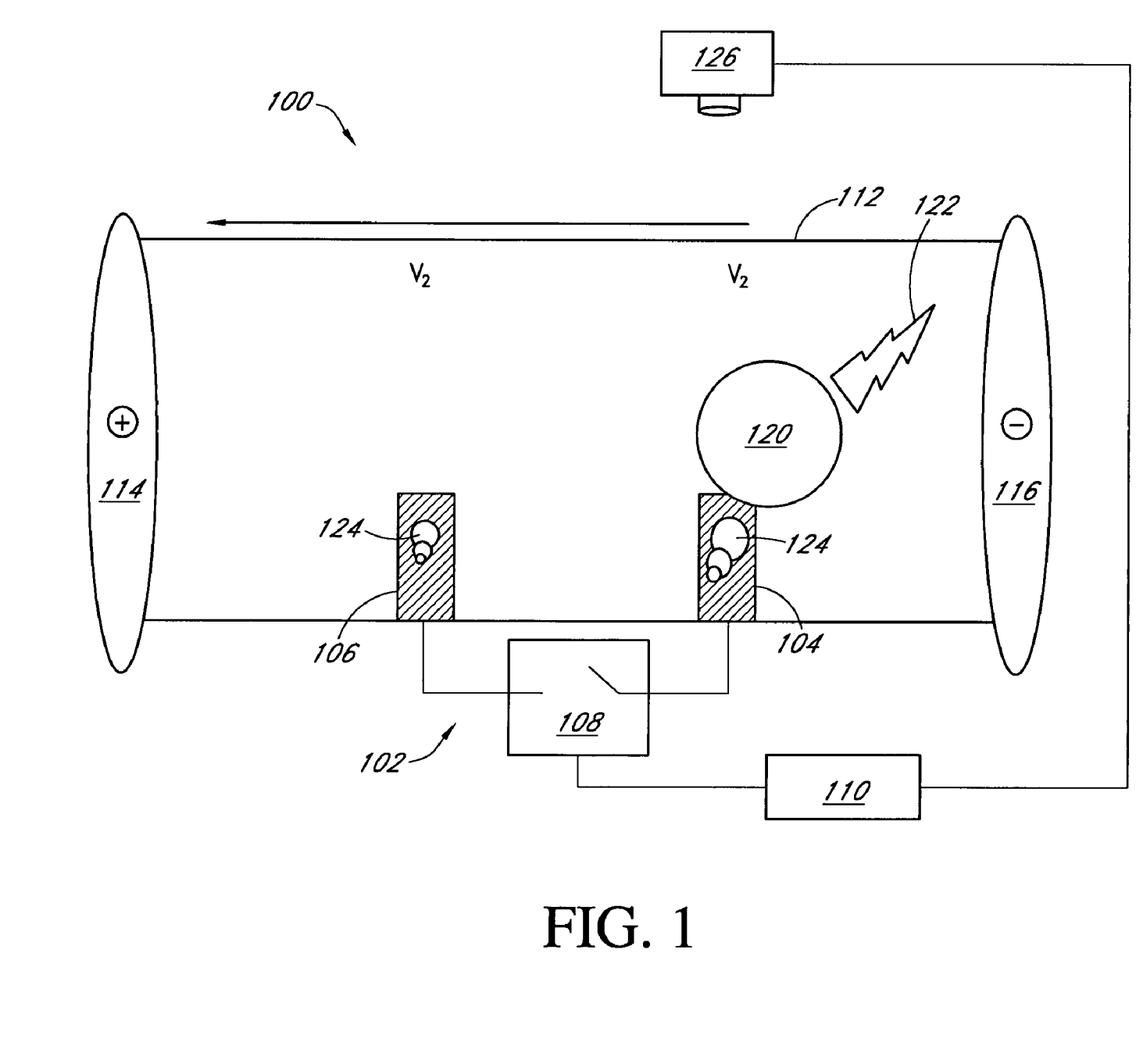
FIG. 1 illustrates an embodiment of an ECL detector in which the disclosed ECL electrode comprises a switch.

FIG. 1 illustrates an embodiment of ECL detector 100 comprising a bipolar ECL electrode 102. In the illustrated embodiment, the ECL detector 100 is a detector for a CE apparatus, although those skilled in the art will understand the detector 100 is useful in other applications, as described in greater detail below. The ECL electrode 102 comprises a first arm 104, a second arm 106, and a switch 108 disposed therebetween. The switch 108 connects the arms 104 and 106 electrically. As such, the switch 108 is not necessarily physically proximate to the arms 104 and 106. The switch 108 is any suitable switch known in the art, including mechanical, electromechanical, and/or solid-state switches, for example. In some embodiments, the switch 108 is under computer or microprocessor 110 control. The arms 104 and 106 are electrically conducting and are fabricated from any suitable material known in the art, including platinum, palladium, gold, valve metal, diamond, carbon, graphite, carbon nanotubes, conductive ceramics, and combinations thereof. Other suitable materials for the arms 104 and 106 are materials that resist bubble formation, which are discussed in greater detail below. In some embodiments, each arm 104 and 106 is fabricated from a different material.

The arms 104 and 106 have any suitable shape, which will depend on factors including the size and shape of the channel 112, the method used to fabricate the arms 104 and 106, the materials from with the arms 104 and 106 are fabricated, and the like. In the illustrated embodiment, the first and second arms 104 and 106 are illustrated as projecting into the channel 112. Those skilled in the art will understand that in other embodiments, the first and second arms 104 and 106 have other shapes, for example, flush with the inner surface of the channel 112. As such, the term "arm" is not intended to define any particular shape. Consequently, the anodic arm 114 and cathodic arm 116 are also referred to herein as the anodic region and cathodic region of the bipolar electrode 102, respectively.

The arms 104 and 106 are disposed in a channel 112. In some embodiments, one or both of the arms 104 and 106 are deposited within the interior of the channel 112, for example, electrochemically. In other embodiments, one or both arms 104 and 106 are deposited in the channel 112 by vapor deposition or by plasma deposition. In some embodiments, one or both of the arms 104 and 106 are fabricated outside the channel 112 and susequently secured in the channel, for example, using an adhesive or by physical means, for example, screws, slots, detents, swaging, tension, and the like. The apparatus 100 further comprises an anode 114 and a cathode 116, which are part of the detector 100 or CE apparatus.

In use, the channel 112 is filled with an electrolyte (not pictured). In some embodiments, the detector is post-capillary. An advantage of such a configuration is that the capillary is independent of the detector, thereby simplifying capillary changes in the instrument. In some embodiments, the detector is pre-capillary which permits detection of, for example, the injection event. In some embodiments, the detector is oncapillary, typically at or near the end from which the analyte of interest exits the capillary. Under electrophoresis conditions, an electric field is applied to the electrolyte by the CE anode 114 and cathode 116. In other embodiments, the detector 100 comprises an anode 114 and a cathode 116, especially when used in non-CE applications, as discussed in greater detail below. The potential of the electrolyte varies with the position in the channel 112. The potential of the electrolyte surrounding arm 104 of the electrode is $V_1$, while the potential around arm 106 is $V_2$. When the switch 108 is closed, the electrode 102 locally shorts the field and assumes an average potential, $\frac{1}{2}(V_1+V_2)$. Accordingly, arm 104 of the electrode is positive (anodic) with respect to the surrounding electrolyte and is also referred to as the anodic arm. Similarly, arm 106 is negative (cathodic) and is also referred to as the cathodic arm. In the illustrated embodiment, this local potential difference initiates the ECL reaction.

In embodiment illustrated in FIG. 1, an ECL-active analyte 120, for example, TBR labeled DNA, is moving in the channel 112 from the cathode 116 towards the anode 114. When the analyte 120 passes over the anodic arm 104, a pulse of light 122 is generated by the ECL reaction. If TPA is in excess or is continuously replenished, the light 122 intensity is proportional to the local concentration of TBR. The light 122 is detected using a photodetector 126 of any type known in the art, for example, photographic film, a photocell, a photomultiplier, or a charge-coupled device (CCD).

As discussed above, distance between the arms 104 and 106 of the floating electrode 102 and the voltage gradient determine the potentials at the anodic 104 and cathodic 106 arms of the electrodes. Capillary electrophoresis is typically performed using capillaries of from about 10 μm to about 100 μm inner diameter, typically from about 25 μm to about 75 μm, and from about 10 cm to about 100 cm long, typically from about 50 cm to about 75 cm, although capillaries of other diameters and lengths are known in the art, and the disclosed apparatus and method are equally applicable to these capillaries. Separation voltages are typically from about 5 kV to about 30 kV. Because the potential drops linearly between the anode and cathode, including the capillary and ECL detector, the minimum distance between the arms of the floating electrode necessary to observe an ECL signal will vary with the redox potentials of the electrochemiluminescent species, the length of the capillary, and the voltage. For example, the oxidation potentials for TPA and TBR are both about 1.1 V, and for water, about 1.2 V. For a 50 cm capillary at 20 kV (400 V/cm), the minimum distance between the arms for TPA/TBR would be about 55 μm [(1.1 V×2)/400 V/cm]. At about 60 μm, water oxidation would be observed, forming $O_2$ at the anodic arm 104, and/or $H_2$ at the cathodic arm 106. Longer floating electrodes are usable over a larger range of capillary lengths, separation voltages, and ECL chemistries. In some embodiments, the distance between the arms of the bipolar electrode is at least about 10 μm, at least about 20 μm, at least about 30 μm, at least about 40 μm, at least about 50 μm, at least about 60 μm, at least about 70 μm, at least about 80 μm, at least about 90 μm, at least about 100 μm, at least about 150 μm, at least about 200 μm, at least about 250 μm, at least about 300 μm, at least about 400 μm, at least about 500 μm, or at least about 1 mm.

The portion of the bipolar electrode 102 within the channel 112, including arms 104 and 106, are dimensioned to fit within the channel 112 while permitting the flow of the electrolyte and analytes within the channel 112. In CE applications, the width of the channel 112 in a detector 100 is typically similar to the inner diameter of the capillary, which is on the order of tens of microns as discussed above. In LC applications, the width of the channel 112 is typically on the order of millimeters. The lengths of the arms 104 and 106 are selected to provide suitable flow in the channel 112, as well as to provide a sufficient ECL signal. The intensity of the ECL signal increases with the area of the arm that is monitored by the photodetector 126. Those skilled in the art will realize that the area of the arm 104 and/or 106 depends on the length and width, as well as on the height, and that these factors are readily varied in order to provide the desired ECL signal output. Consequently, the performance and sensitivity of the photodetector 126 are factors used in determining the dimensions of the arms 104 and/or 106. In some embodiments, the lengths and widths of each arm 104 and 106 are independently from about 10 µm to about 100 µm. Furthermore, in some embodiments, one or both of the arms 104 and 106 or another portion of the bipolar electrode 102 comprises indicia or is formed in a shape that facilitates the optical alignment of the bipolar electrode 102 with the photodetector 126, for example a bulls-eye or a cross.

Those skilled in the art will understand that the disclosed apparatus and method is useful for any ECL reagents or systems known in the art, and that the TPA/TBR system exemplified herein, is merely illustrative. Those skilled in the art realize that other ruthenium bipyridyl systems are useful as electrochemiluminescent reagents, as are other transition metal species known in the art. Examples of other ECL systems include luminol and acridan ester systems. Other suitable ECL systems are disclosed in U.S. patent application Ser. No. 10/713,479, filed on Nov. 14, 2003. Those skilled in the art will also understand that, in some embodiments, the ECL reaction occurs at the anodic arm, the cathodic arm, or both, depending on the particular system. Consequently, the importance of bubble formation and/or accumulation of charged species on a particular arm of the bipolar electrode depends, in part, on which arm the ECL occurs. For example, bubble formation at the arm at which the ECL reaction of interest occurs is more likely to interfere with the detection of the reaction than bubble formation at the other arm. Similarly, accumulation of charged ECL-active species on or around the arm at which the ECL reaction of interest occurs is likely to generate an undesired background signal.

Those skilled in the art will understand that, in some embodiments, the species of interest, that is, the analyte, is electrochemiluminescent. In other embodiments, an ECL label or tag is attached to the species of interest, for example, a biomolecule, a piece of DNA, a polypeptide, or the like. In some embodiments, the ECL label is covalently attached to the species of interest. In some embodiments, the ECL label is not covalently attached to the species of interest. For example, in some embodiments, TBR intercalates double-stranded DNA. Consequently, the label is referred to herein using the same term whether it is covalently or non-covalently attached to the species of interest. For example, the terms "TBR" and "tris-(2,2'-bipyridyl)ruthenium$^{+3}$" as used herein refer both to covalently modified versions of the compound as well as the parent compound.

The bipolar electrode 102 is useful in any type of ECL detector using a bipolar electrode. In some embodiments, the ECL detector is used in a CE apparatus. The ECL detector is useful in any type of CE apparatus, for example, capillary zone electrophoresis (CZE), capillary gel electrophoresis, capillary isoelectric focusing (cIEF), micellar electrokinetic chromatography (MEKC), isotachophoresis, or capillary electrochromatography (CEC). In some embodiments, the bipolar electrode 102 is used in an ECL detector for another type of apparatus, for example, an apparatus that separates and/or identifies a compound using a mechanical pump to force a solution of the compound through a column selected separate the compound of interest. Examples of such apparatus include liquid chromatography (LC), high performance (pressure) liquid chromatography (HPLC), medium pressure liquid chromatography (MPLC), fast performance (protein) liquid chromatography (FPLC) systems, and the like. As discussed above, in some embodiments, the detector is post-column, pre-coluni, or on-column.

Figure 2:
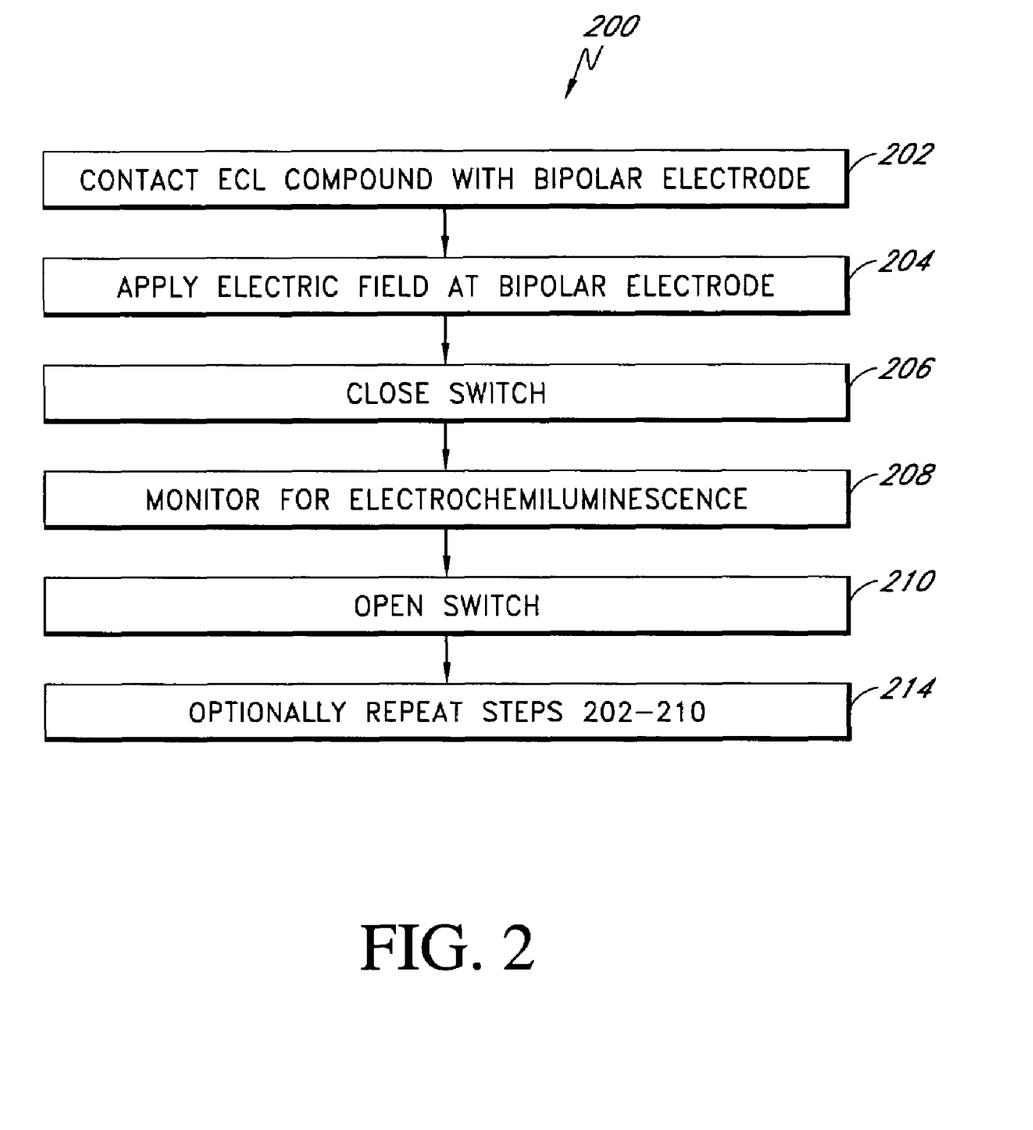
FIG. 2 is a flowchart illustrating an embodiment of a method for ECL detection using the bipolar electrode illustrated in FIG. 1.

Also provided is a method for detecting an electrochemiluminescent molecule or analyte, an embodiment 200 of which is illustrated in FIG. 2. The following description is made with reference to the apparatus illustrated in FIG. 1. In step 202, an electrochemiluminescent molecule 120 is contacted with the bipolar electrode 102. In step 204, an electric field sufficient to initiate an electrochemiluminescent reaction at the bipolar electrode 102 is applied. In step 206, the switch 108 is closed, thereby electrically connecting arms 104 and 106. In step 208, the system is monitored for electrochemiluminescence. In step 210, the switch 108 is opened. In step 214, steps 202-210 are optionally repeated.

In some embodiments, the analyte 120 is contacted with the electrode 102 in step 202 using CE. In embodiments in which the bipolar electrode is used in a CE detector, the electric field in step 204 is applied substantially during the entire detection process using anode 114 and cathode 116. On opening the switch 108, the arms 104 and 106 are electrically disconnected. Accordingly, the potential of each arm 104 and 106 is the same as the potential of the surrounding electrolyte and no electrochemistry occurs at the electrode 102. When the switch 108 is closed, the bipolar electrode 102 behaves as described above. The ECL measurement is acquired when the switch 108 is closed. In effect, the switch 108 allows a user to switch the bipolar electrode 102 off and on. Switching the bipolar electrode 102 off and on permits a user, first, to control the duty cycle of the bipolar electrode, thereby minimizing bubble 124 formation on the electrode 102, and second, to release any charged species from the zero-field region around the electrode 102, thereby reducing the background light signal. As discussed above, when the switch 108 is closed, the electric field around the bipolar electrode 102 is reduced, thereby slowing the migration of charged species, and thereby permitting their accumulation on or around the bipolar electrode 102. Because the potential at the arms 104 and 106 is the same as the local potential when the switch 108 is opened, charged species are released from the arms 104 and 106.

The cycle for opening and closing the switch 108 will depend on the propensity for bubble formation at the bipolar electrode 102 under the analytical conditions and/or the build-up of undesired charged species on or around the bipolar electrode 102. These factors themselves depend on variable well known in the art, including the concentration of the analyte, the efficiency of the ECL reaction, the effective potential of the bipolar electrode 102, the composition of the bipolar electrode 102, and the like. In some embodiments, a factor used in the determination of the switching cycle is the time used to acquire the ECL signal, for example, the integration time of the photodetector. In some embodiments, the switch 108 is closed (on) during data acquisition and open (off) otherwise. Those skilled in the art will realize that the particular times depend on the characteristics of the photodetector. In some embodiments, the switch is closed for from about 100 ms to about 1 s. In some embodiments, the switch is open for from about 10 ms to about 100 ms. In some embodiments, the switch 108 is controlled by a computer, a microprocessor, or a microcontroller 110, which may also be used to control other parameters in the CE system, for example, the potential between the CE electrodes 114 and 116, the photodetection system 126, a data acquisition system, sample handling and/or tracking, and the like.

Figure 3:
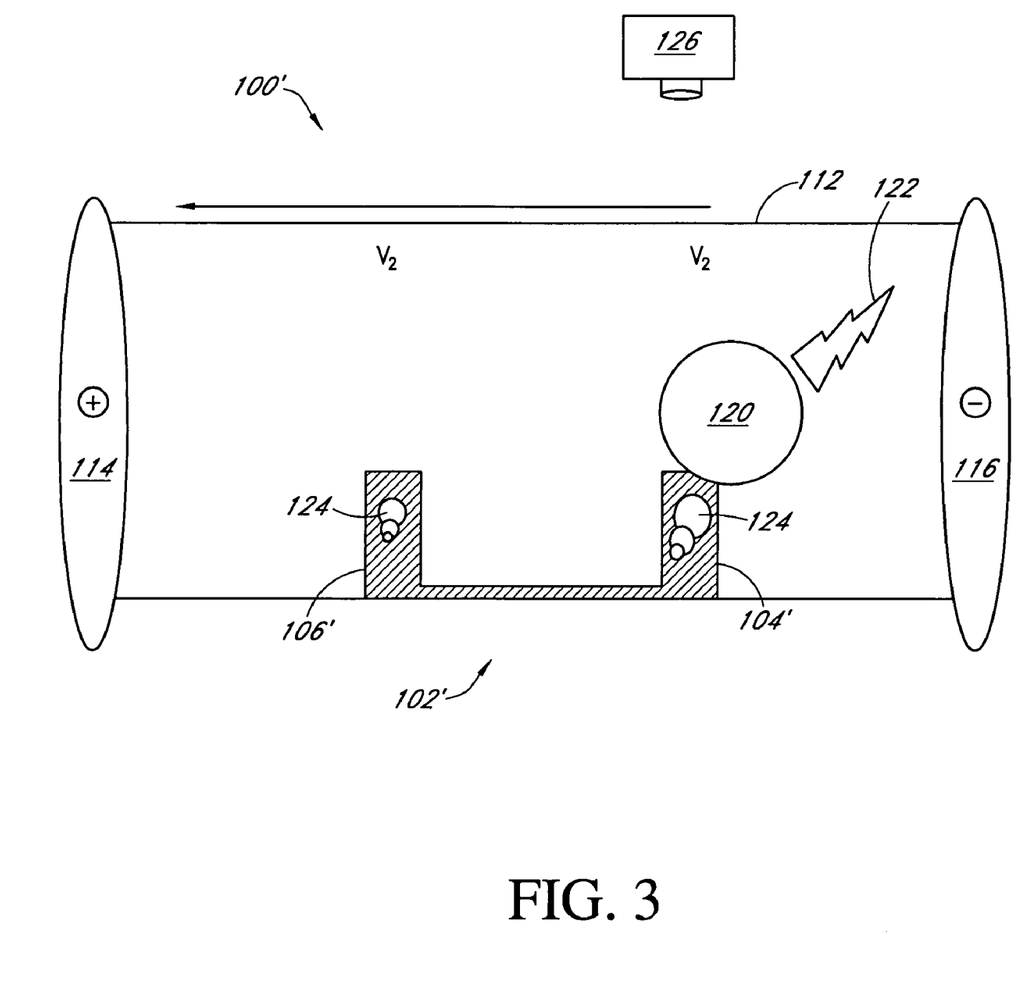
FIG. 3 illustrates another embodiment of an ECL detector comprising an ECL electrode fabricated from a material that resists bubble formation.

In other embodiments, the material from which the bipolar electrode is fabricated is selected to overcome the problems of bubbles accumulating on the electrode by either of two mechanisms, or a combination thereof. FIG. 3 illustrates an embodiment of an ECL detector 100'. Components similar to those illustrated in FIG. 1 are indicated by like reference numbers. ECL detector 100' comprises a U-shaped bipolar electrode 102' that is suitably made from a material that resists bubble formation. Those skilled in the art will understand that other shapes are useful for the bipolar electrode 102'. In some embodiments, each arm 104' and 106' is fabricated from a different material. Dimensions and applications for the bipolar electrode 102' are similar to those described above for bipolar electrode 102.

One class of electrode material has a large potential window in the analytical medium. As used herein, the "potential window" of an electrode material in a particular medium is the range of potentials under which electrochemical reactions of the medium that interfere with desired electrochemical reactions do not occur. An electrode with a larger potential window permits the use of a wider range of ECL-active compounds because different compounds undergo ECL at different potentials. Those skilled in the art will understand that the potential window for a particular electrode material depends on the medium as well as the characteristics of the desired electrochemical reaction. In an aqueous medium, a large potential window is at least about 1.5 V or at least about 2 V. For example, in an aqueous medium, the oxidation potential for the ECL compound at the electrode 102' is ideally below the oxidation potential of water. Accordingly, no appreciable electrolysis of water occurs at the bipolar electrode 102', and consequently bubble 124 formation is reduced. An example of such an electrode material for aqueous media is electrically conducting or semiconducting diamond. Electrodes made from electrically conducting or semiconducting diamond are referred to as diamond electrodes herein. Boron-doped diamond is an example of an electrically conducting diamond material. The fabrication of boron-doped diamond electrodes is described, for example in U.S. Pat. Nos. 6,267,866, 5,900,127, 5,776,323, and 5,399,247, the disclosures of which are incorporated by reference. A comparison of the potential window of a diamond electrode and a platinum electrode is provided in EXAMPLE 1 below. An additional advantage of diamond electrodes is that photogeneration for the ECL-reaction is efficient, thereby providing a more sensitive system.

A second class of electrode material physisorbs or chemisorbs the oxygen, hydrogen, and/or other gases generated by the electrolysis of the medium. Physisorption or physical absorption is the absorption of a compound to a substrate in which the attractive forces between the compound and substrate are intermolecular, for example, van der Waals forces. Chemisorption or chemical absorption is the absorption of a compound to a substrate in which the attractive forces between the compound and the substrate are chemical, that is, involving the valance electrons. Using hydrogen as an example, in an electrode fabricated from a material that physisorbs or chemisorbs hydrogen gas formed at the electrode, the hydrogen is absorbed onto and/or into the electrode itself, and consequently, does not form bubbles on the surface of the electrode.

About 50 metallic elements are known to absorb significant amounts of hydrogen. An example of such a material is palladium, as described in U.S. patent application Ser. No. 09/938,947, filed Aug. 24, 2001, the disclosure of which is incorporated by reference. Other examples include copper and nickel. Carbon nanotubes are also known to chemisorb hydrogen. A number of materials are known to absorb hydrogen as hydrides, for example, $MgH_2$, $Mg_2NiH_4$, $FeTiH_2$, and $LaNi_5H_6$. The hydrogen storage alloys in common use occur in four different forms: $AB_5$ (e.g., $LaNi_5$), AB (e.g., FeTi), $A_2B$ (e.g., $Mg_2Ni$) and $AB_2$ (e.g., $ZrV_2$).

Some metal oxides, for example, some ceramic materials are useful as electrodes and also absorb oxygen. Examples include binary oxides, perovskites, and spinels. Suitable compounds are stoichiometric or non-stoichiometric. Other suitable electrode materials are metal hydrous oxides or hydroxides, for example, nickel(II) hydroxide. An example of an electrode material that reversibly reacts with oxygen is lead.

In some embodiments, the cathodic arm and anodic arm of the bipolar electrode are fabricated from different materials, for example, the cathodic arm is fabricated from a hydrogen absorbing material, anodic arm from an oxygen absorbing material.

Figure 4:
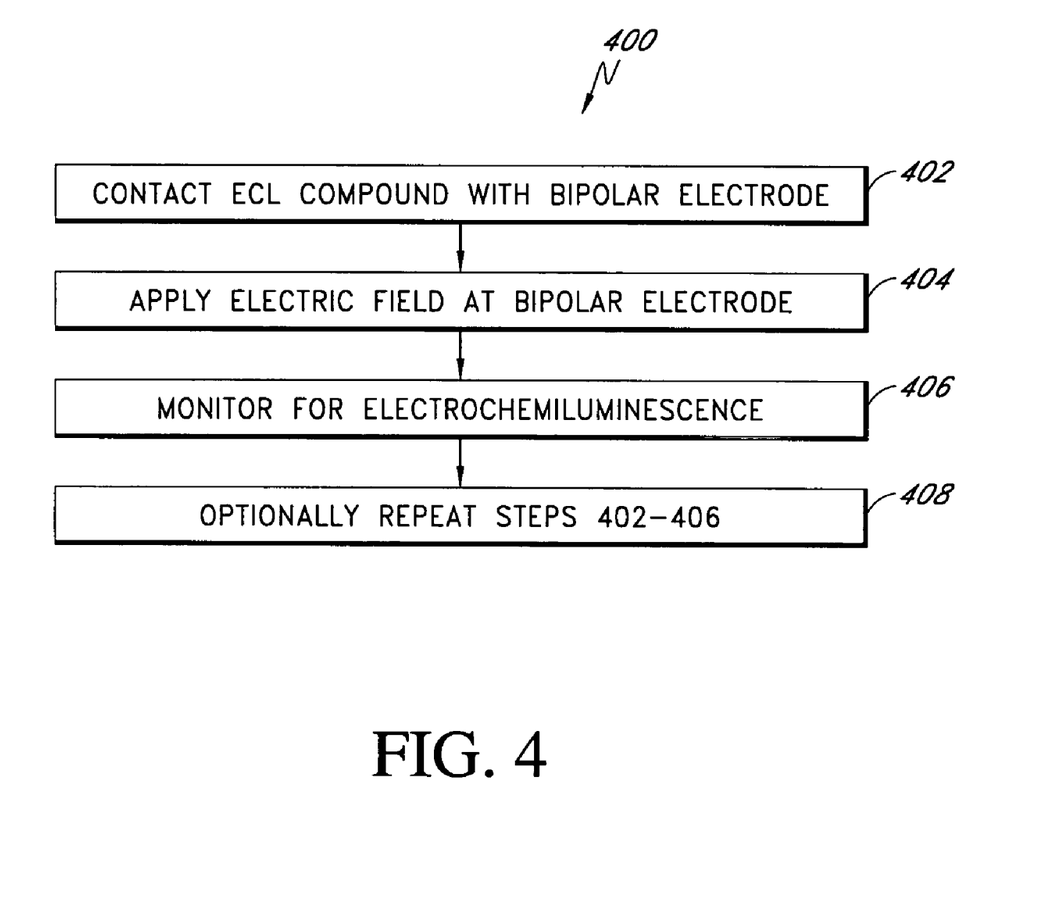
FIG. 4 is a flowchart illustrating an embodiment of a method for ECL detection using the bipolar electrode illustrated in FIG. 3.

FIG. 4 is a flowchart of method 400 for ECL detection with reference to the apparatus illustrated in FIG. 3. In step 402, an electrochemiluminescent molecule 120 is contacted with the bipolar electrode 102'. In step 404, an electric field sufficient to initiate an electrochemiluminescent reaction at the bipolar electrode 102 is applied. In step 406, the system is monitored for electrochemiluminescence 122. In step 408, steps 402-406 are optionally repeated.

EXAMPLE 1

Figure 5:
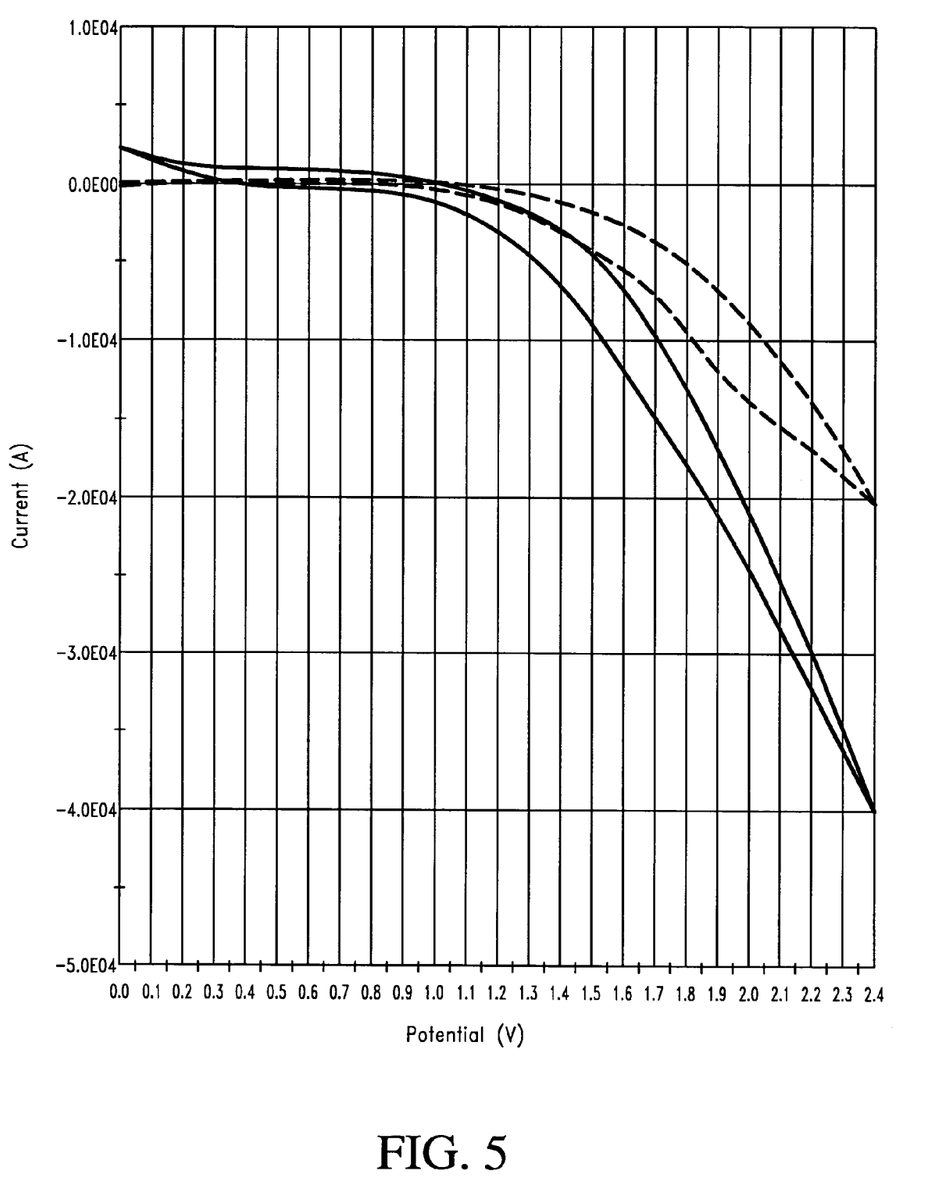
FIG. 5 provides cyclic voltammograms for platinum and diamond electrodes illustrating the potential windows for the electrodes.

Cyclic voltammograms (CV) for platinum (solid) and diamond (dashed) electrodes in 1× Genetic Analysis buffer (1× GA buffer, Applied Biosystems, Foster City, Calif.) are provided in FIG. 5. As the potential is varied from 0 V to 2.4 V, the current for the platinum electrode ranges from about 0.25× $10^{-4}$ A to about −4× $10^{-4}$ A, respectively. For the diamond electrode, the current goes from about 0 A to about −2× $10^{-4}$ A for the same potential window, illustrating the larger potential window for a diamond electrode. The larger potential window indicates that the diamond electrode is compatible with a larger number of ECL-active analytes than the platinum electrode in this medium.

EXAMPLE 2

Figure 6:
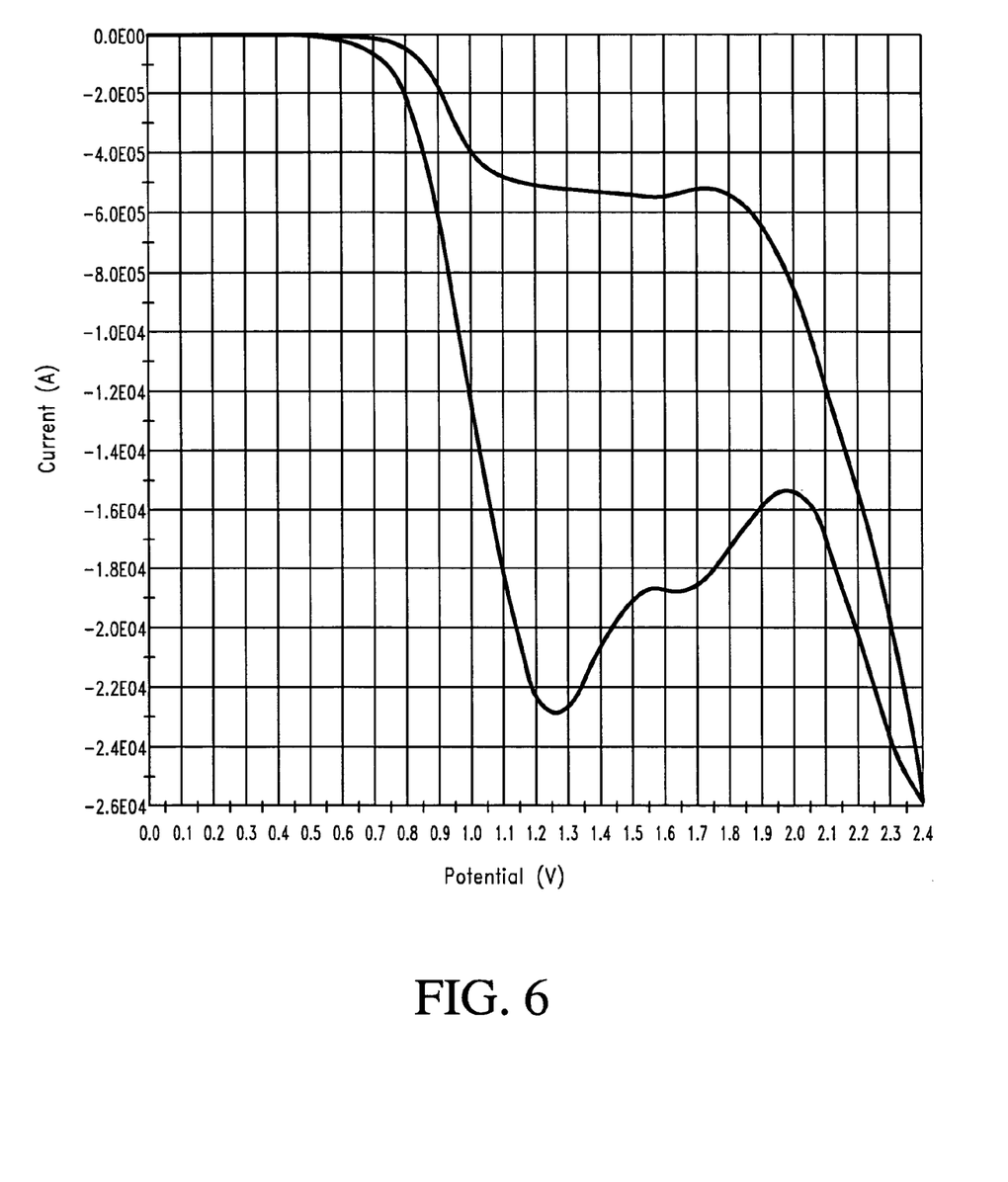
FIG. 6 provides a cyclic voltammogram of 100 µM TBR in 100 mM TPA in 1× GA buffer using a diamond electrode.

FIG. 6 is a cyclic voltammogram of 100 µM TBR and 100 mM TPA in 1× GA buffer, after background current (1× GA buffer) subtraction using a diamond electrode, illustrating the large potential window available using a diamond electrode. In this example, the usable potential window of the diamond electrode extends to about 2 V. The additional features in the CV compared to the diamond electrode CV illustrated in FIG. 5 illustrate the electrochemical reaction of the TBR and TPA.

EXAMPLE 3

Although the switch for bipolar electrode may be used independently of the improved electrode materials, we have discovered that using the two techniques concurrently provides improved results, as illustrated in the following experiment.

Figure 7A:
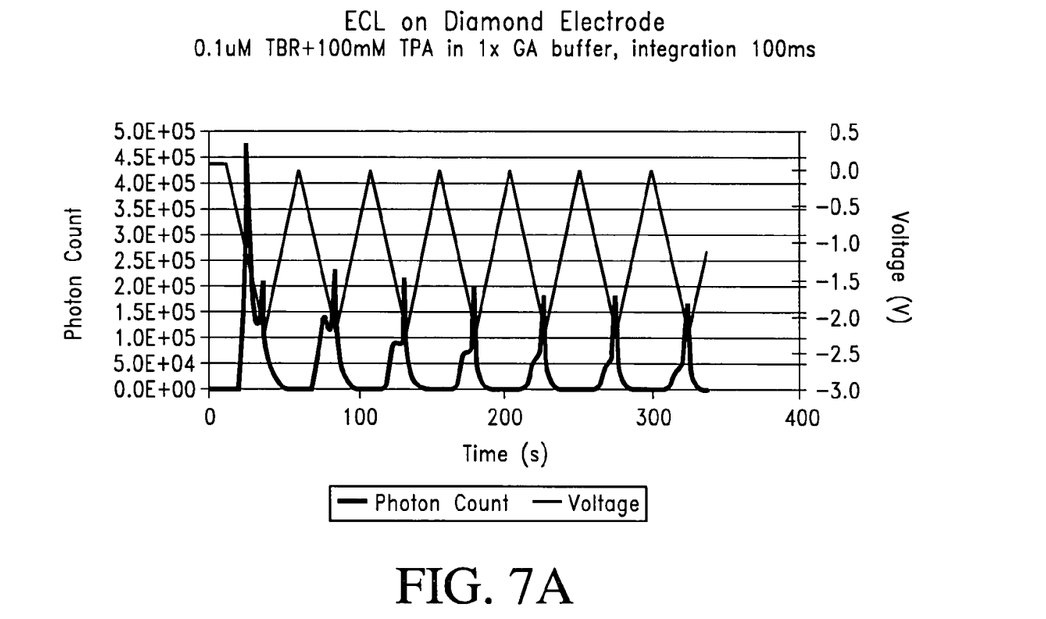
FIG. 7A and FIG. 7B provide ECL results using an embodiment of the bipolar electrode illustrated in FIG. 1. The electrodes are fabricated from diamond and platinum, respectively.
Figure 7B:
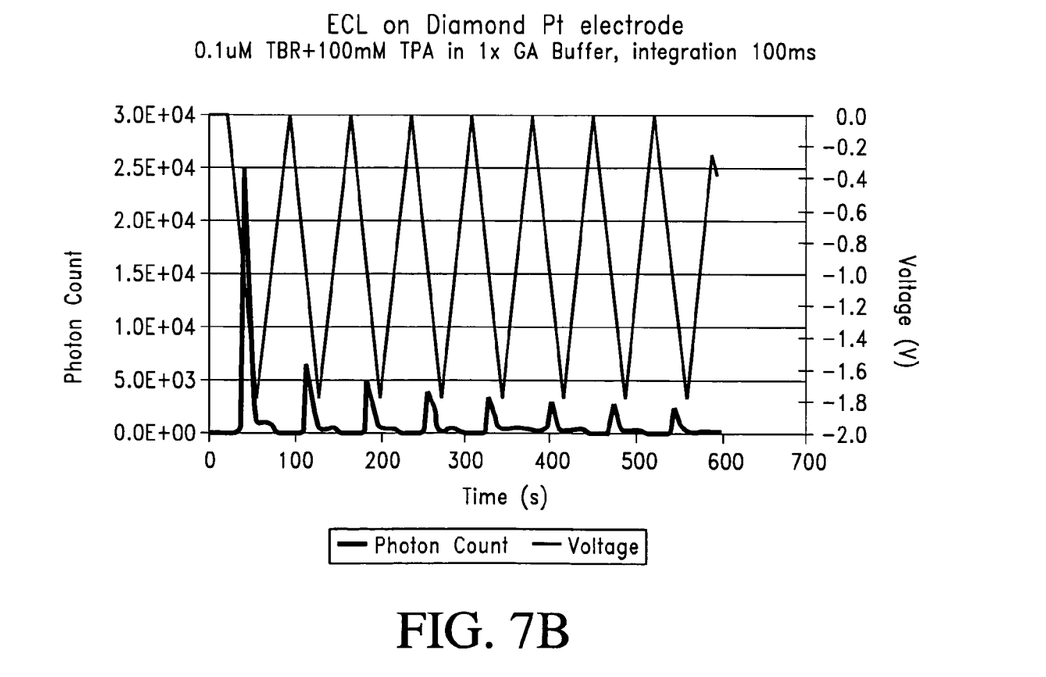

FIG. 7A and FIG. 7B are experimental results comparing ECL on diamond and platinum electrodes, respectively. The experimental conditions for both electrode materials were: 0.1 µM TBR, 100 mM TPA in 1× GA buffer, 100 ms integration. The switch and photodetector were controlled using a personal computer equipped with a data acquisition and control card and software (LabVIEW® National Instruments). In this example, the cycle for the switch was 100 ms closed and 10 ms open. The data was acquired while the switch was closed. A larger potential was applied in the diamond electrode experiment (−2.5 V) than in the platinum electrode experiment (−1.8 V) reflecting the larger potential window. The photon count for the diamond electrode was at least 20 times greater for each redox cycle than for the platinum electrode, and was more reproducible.

The embodiments illustrated and described above are provided as examples only. Various changes and modifications can be made to the embodiments presented herein by those skilled in the art without departure from the spirit and scope of the teachings herein.

What is claimed is:

1. A method for detecting an electrochemiluminescent analyte comprising:
    (a) contacting an electrochemiluminescent analyte with a bipolar electrode, wherein the bipolar electrode comprises an electrically conductive first arm, an electrically conductive second arm, and an electrical switch disposed therebetween;
    (b) applying an electric field sufficient to initiate an electrochemiluminescent reaction in the analyte at the bipolar electrode;
    (c) closing the switch;
    (d) monitoring for electrochemiluminescence from the analyte;
    (e) opening the switch; and
    (f) repeating at least steps (c) through (e);
    wherein the switch is closed and opened in a cycle that inhibits bubble formation on at least one of the first arm or the second arm.

2. The method of claim 1, wherein the electrochemiluminescent analyte is contacted with the bipolar electrode using a capillary electrophoresis apparatus.

3. The method of claim 2, wherein the electric field is applied using the capillary electrophoresis apparatus.

4. The method of claim 2, wherein the capillary electrophoresis apparatus further comprises a photodetector for monitoring for electrochemiluminescence.

5. The method of claim 1, wherein the electrochemiluminescent analyte comprises tris-(2,2'-bipyridyl)ruthenium$^{+3}$.

6. The method of claim 5, further comprising contacting the tris-(2,2'-bipyridyl)ruthenium$^{+3}$ with tripropylamine radical.

7. The method of claim 1, wherein the switch is controlled by a microprocessor or a microcontroller.

8. The method of claim 1, wherein the distance between the first arm and the second arm is at least about 20 μm.

9. The method of claim 1, wherein at least one of the first arm or the second arm comprises platinum.

10. The method of claim 1, wherein at least one of the first arm or the second arm comprises a material that resists bubble formation.

11. The method of claim 10, wherein the potential window for the material in aqueous medium is at least about 1.5 V.

12. The method of claim 11, wherein the material is boron-doped diamond.

13. The method of claim 10, wherein the material absorbs hydrogen.

14. The method of claim 13, wherein the material is palladium.

15. The method of claim 10, wherein the material is a metal oxide that absorbs oxygen.

16. A method for detecting an electrochemiluminescent analyte comprising:
    (a) contacting an electrochemiluminescent analyte with a bipolar electrode, wherein the bipolar electrode comprises an electrically conductive first arm, an electrically conductive second arm, and an electrical switch disposed therebetween;
    (b) applying an electric field sufficient to initiate an electrochemiluminescent reaction in the analyte at the bipolar electrode;
    (c) closing the switch;
    (d) monitoring for electrochemiluminescence from the analyte;
    (e) opening the switch; and
    (f) repeating at least steps (c) through (e);
    wherein the switch is closed and opened in a cycle that releases charged species accumulated on or around at least one of the first arm or the second arm.

17. The method of claim 16, wherein the electrochemiluminescent analyte is contacted with the bipolar electrode using a capillary electrophoresis apparatus.

18. The method of claim 17, wherein the electric field is applied using the capillary electrophoresis apparatus.

19. The method of claim 17, wherein the capillary electrophoresis apparatus further comprises a photodetector for monitoring for electrochemiluminescence.

20. The method of claim 16, wherein the electrochemiluminescent analyte comprises tris-(2,2'-bipyridyl)ruthenium$^{+3}$.

21. The method of claim 20, further comprising contacting the tris-(2,2'-bipyridyl)ruthenium$^{+3}$ with tripropylamine radical.

22. The method of claim 16, wherein the switch is controlled by a microprocessor or a microcontroller.

23. The method of claim 16, wherein the distance between the first arm and the second arm is at least about 20 μm.

24. The method of claim 16, wherein at least one of the first arm or the second arm comprises platinum.

25. The method of claim 16, wherein at least one of the first arm or the second arm comprises a material that resists bubble formation.

26. The method of claim 25, wherein the potential window for the material in aqueous medium is at least about 1.5 V.

27. The method of claim 26, wherein the material is boron-doped diamond.

28. The method of claim 25, wherein the material absorbs hydrogen.

29. The method of claim 28, wherein the material is palladium.

30. The method of claim 25, wherein the material is a metal oxide that absorbs oxygen.

* * * * *